United States Patent
Fujii et al.

(10) Patent No.: US 7,029,629 B2
(45) Date of Patent: Apr. 18, 2006

(54) COMPUTERIZED METHOD AND APPARATUS FOR ANALYZING AMINO ACIDS

(75) Inventors: Yoshio Fujii, Hitachinaka (JP); Masahito Ito, Hitachinaka (JP); Kimiyoshi Koda, Hitachinaka (JP)

(73) Assignee: Hitachi, LTD, (JP)

( * ) Notice: Subject to any disclaimer, the term of this patent is extended or adjusted under 35 U.S.C. 154(b) by 0 days.

(21) Appl. No.: 10/982,882

(22) Filed: Nov. 8, 2004

(65) Prior Publication Data

US 2005/0090012 A1    Apr. 28, 2005

Related U.S. Application Data

(63) Continuation of application No. 09/879,165, filed on Jun. 13, 2001.

(30) Foreign Application Priority Data

Sep. 1, 2000    (JP) .............................. 2000-269864

(51) Int. Cl.
*G01N 33/00*    (2006.01)
(52) U.S. Cl. ..................... 422/68.1; 422/58; 422/59; 422/63
(58) Field of Classification Search ............... 422/68.1, 422/63, 58, 59
See application file for complete search history.

(56) References Cited

U.S. PATENT DOCUMENTS

| | | | |
|---|---|---|---|
| 3,649,203 A | 3/1972 | Schneider | |
| 4,133,753 A | 1/1979 | Takeuchi et al. | |
| 4,959,176 A | 9/1990 | Slocum et al. | |
| 5,236,847 A | 8/1993 | Satake et al. | |
| 5,827,426 A | 10/1998 | Fujii et al. | |

FOREIGN PATENT DOCUMENTS

| | | |
|---|---|---|
| JP | 53-060291 | 5/1978 |
| JP | 59-010849 | 1/1984 |
| JP | 04-194570 | 7/1992 |
| JP | 09-080037 | 3/1997 |

OTHER PUBLICATIONS

Kimie Murayama et al; "Resolution ot 52 Ninhydrin-positive compounds with a high-speed amino acid analyzer"; Journal of Chromatography, 224 (1981) pp. 315-321; Elsevier Scientific Publishing Company-Amsterdam.

Jacques le Boucher et al.;"Amino Acid determination in biological fluids by automated ion-exchange chromatography; performance of Hitachi L-8500A"; Clinical Chemistry 43:8, (1997) pp. 1421-1428.

*Primary Examiner*—Monique T. Cole
(74) *Attorney, Agent, or Firm*—Dickstein Shapiro Morin & Oshinsky LLP

(57) ABSTRACT

A method for analyzing a plurality of amino acids in a fluid sample by a user is provided comprising the steps of introducing the sample into a buffer solution, passing the sample in the buffer solution through a separation column and setting a lithium ion concentration in the buffer to no more than 0.3 mols/L up to a time before β-aminoisobutyric acid (β-AiBA) is eluted.

11 Claims, 15 Drawing Sheets

FIG. 3

| TIME (min) | %B1 | %B2 | %B3 | %B4 | %B5 | TEMPERATURE (°C) | FLOW RATE 1 (ml/min) | %R1 | %R2 | %R3 | FLOW RATE 2 (ml/min) |
|---|---|---|---|---|---|---|---|---|---|---|---|
| 0.0 | 100.0 | 0.0 | 0.0 | 0.0 | 0.0 | 38 | 0.350 | 50.0 | 50.0 | 0.0 | 0.300 |
| 2.0 | 100.0 | 0.0 | 0.0 | 0.0 | 0.0 | 35 | | | | | |
| 20.0 | 100.0 | 0.0 | 0.0 | 0.0 | 0.0 | | | | | | |
| 20.0 | 80.0 | 20.0 | 0.0 | 0.0 | 0.0 | 60 | | | | | |
| 45.0 | 80.0 | 20.0 | 0.0 | 0.0 | 0.0 | 70 | | | | | |
| 55.0 | | | | | | 40 | | | | | |
| 73.0 | | | | | | 70 | | | | | |
| 84.0 | 15.0 | 75.0 | 10.0 | 0.0 | 0.0 | | | | | | |
| 85.0 | | | | | | 63 | | | | | |
| 92.0 | 15.0 | 75.0 | 10.0 | 0.0 | 0.0 | | | | | | |
| 92.1 | 0.0 | 60.0 | 40.0 | 0.0 | 0.0 | | | | | | |
| 105.0 | | | | | | 70 | | | | | |
| 117.0 | 0.0 | 20.0 | 0.0 | 80.0 | 0.0 | | | | | | |
| 117.1 | 0.0 | 25.0 | 0.0 | 75.0 | 0.0 | | | | | | |
| 130.0 | 0.0 | 25.0 | 0.0 | 75.0 | 0.0 | | | | | | |
| 130.1 | 0.0 | 0.0 | 0.0 | 100.0 | 0.0 | | | | | | |
| 145.0 | 0.0 | 0.0 | 0.0 | 100.0 | 0.0 | | | | | | |
| 145.1 | 0.0 | 0.0 | 0.0 | 0.0 | 100.0 | | | | | | |
| 149.0 | | | | | | | | 50.0 | 50.0 | 0.0 | |
| 149.1 | | | | | | | | 0.0 | 0.0 | 100.0 | |
| 153.0 | 0.0 | 0.0 | 0.0 | 0.0 | 100.0 | | | | | | |
| 153.1 | 100.0 | 0.0 | 0.0 | 0.0 | 0.0 | | | | | | |
| 155.0 | | | | | | 38 | | | | | |
| 159.0 | | | | | | | | 0.0 | 0.0 | 100.0 | |
| 159.1 | | | | | | | | 50.0 | 50.0 | 0.0 | |
| 178.0 | 100.0 | 0.0 | 0.0 | 0.0 | 0.0 | | | | | | |

FIG. 4

| TIME (min) | %B1 | %B2 | %B3 | %B4 | %B5 | TEMPER-ATURE(°C) | FLOW RATE 1 (ml/min) | %R1 | %R2 | %R3 | FLOW RATE 2 (ml/min) |
|---|---|---|---|---|---|---|---|---|---|---|---|
| 0.0 | 100.0 | 0.0 | 0.0 | 0.0 | 0.0 | 38 | 0.350 | 50.0 | 50.0 | 0.0 | 0.300 |
| 2.0 | 100.0 | 0.0 | 0.0 | 0.0 | 0.0 | 33 | | | | | |
| 21.5 | 100.0 | 0.0 | 0.0 | 0.0 | 0.0 | | | | | | |
| 21.6 | 80.0 | 20.0 | 0.0 | 0.0 | 0.0 | 62 | | | | | |
| 33.5 | 70.0 | 30.0 | 0.0 | 0.0 | 0.0 | | | | | | |
| 33.6 | 10.0 | 90.0 | 0.0 | 0.0 | 0.0 | | | | | | |
| 36.5 | 10.0 | 90.0 | 0.0 | 0.0 | 0.0 | 40 | | | | | |
| 43.5 | 10.0 | 90.0 | 0.0 | 0.0 | 0.0 | | | | | | |
| 43.6 | 0.0 | 100.0 | 0.0 | 0.0 | 0.0 | | | | | | |
| 50.5 | 0.0 | 100.0 | 0.0 | 0.0 | 0.0 | 70 | | | | | |
| 50.6 | 0.0 | 0.0 | 100.0 | 0.0 | 0.0 | | | | | | |
| 68.4 | 0.0 | 0.0 | 100.0 | 0.0 | 0.0 | 45 | | | | | |
| 69.5 | 0.0 | 0.0 | 100.0 | 0.0 | 0.0 | | | | | | |
| 69.6 | 60.0 | 0.0 | 0.0 | 40.0 | 0.0 | | | | | | |
| 75.0 | 60.0 | 0.0 | 0.0 | 40.0 | 0.0 | | | | | | |
| 75.1 | 0.0 | 0.0 | 0.0 | 100.0 | 0.0 | | | | | | |
| 82.0 | 0.0 | 0.0 | 0.0 | 100.0 | 0.0 | | | | | | |
| 82.1 | 0.0 | 20.0 | 0.0 | 80.0 | 0.0 | | | | | | |
| 92.5 | 0.0 | 20.0 | 0.0 | 80.0 | 0.0 | 70 | | | | | |
| 99.5 | 0.0 | 20.0 | 0.0 | 80.0 | 0.0 | | | | | | |
| 99.6 | 0.0 | 0.0 | 0.0 | 100.0 | 0.0 | | | | | | |
| 112.5 | 0.0 | 0.0 | 0.0 | 100.0 | 0.0 | | | | | | |
| 112.6 | 0.0 | 0.0 | 0.0 | 0.0 | 100.0 | | | | | | |
| 116.0 | 0.0 | 0.0 | 0.0 | 0.0 | 100.0 | | | 50.0 | 50.0 | 0.0 | |
| 116.1 | 0.0 | 0.0 | 0.0 | 0.0 | 100.0 | | | 0.0 | 0.0 | 100.0 | |
| 121.5 | 0.0 | 0.0 | 0.0 | 0.0 | 100.0 | | | | | | |
| 121.6 | 100.0 | 0.0 | 0.0 | 0.0 | 0.0 | | | | | | |
| 125.0 | 100.0 | 0.0 | 0.0 | 0.0 | 0.0 | 38 | | | | | |
| 126.0 | 100.0 | 0.0 | 0.0 | 0.0 | 0.0 | | | 0.0 | 0.0 | 100.0 | |
| 126.1 | 100.0 | 0.0 | 0.0 | 0.0 | 0.0 | | | 50.0 | 50.0 | 0.0 | |
| 148.0 | 100.0 | 0.0 | 0.0 | 0.0 | 0.0 | | | | | | |

(A) THREE SOLUTION GRADIENT (B) TWO SOLUTION GRADIENT

COMPUTERIZED METHOD AND APPARATUS FOR ANALYZING AMINO ACIDS

CROSS REFERENCE TO RELATED APPLICATION

The present application is a continuation application of U.S. patent application Ser. No. 09/879,165, filed on Jun. 13, 2001, the disclosure of which is incorporated herein by reference in its entirety.

FIELD OF THE INVENTION

This invention relates to a computerized method and apparatus for analyzing amino acids suited for application, for example, in the clinical field.

DISCUSSION OF THE RELATED ART

Amino acid analyzers can be broadly classified into those used to carry out a standard analyzing method of analyzing about 20 components of protein-hydrolyzed amino acids and also to carry out a body fluid analyzing method wherein about 40 components of amino acid analogue substances in the body fluid are analyzed. The body fluid analyzing method is described herein, i.e., an analyzing method wherein a body fluid such as a serum, urine, a cerebrospinal fluid or the like is analyzed for clinical use in order to diagnose diseases and serve for medical treatment.

As a conventional example of body fluid analysis, there are known Japanese Laid-open Patent Publication No. Sho 53-60291, Japanese Laid-open Patent Publication No. Sho 59-10849, Japanese Laid-open Patent Publication No. Hei 4-194570 and Japanese Laid-open Patent Publication No. Hei 9-80037. Publications, including, Journal of Chromatography, 224; 315–321 (1981), entitled, "Resolution of 52 ninhydrin-positive compounds with a High-speed amino acid analyzer" and Clinical Chemistry 43; 8, 1421–1428 (1997), entitled "Amino Acid determination in biological fluids by automated ion-exchange chromatography: performance of Hitachi L-8500A" are known.

These known body fluid analyzing methods are similar with respect to a series of analyzing procedures including mixing a plurality of buffer solutions, adding a sample to the mixed buffer solution, and passing through a separation column for detection. Modifications of the separation column and a flow rate of the buffer solution permit a faster analyzing time with age, so that the analysis can be now accomplished in 110 minutes for ordinary purposes, and in 90–60 minutes with the case of high-speed analysis.

According to the body fluid analysis, about 40 components as mentioned above (strictly speaking, 41 components not marked with "*" in Table 1) can be analyzed at the same time. In recent years, however, it has been found that components that have never been intended for analysis up to now are effective for checking a specific type of disease. Thus, there is an increasing demand for analyzing, aside from the above 41 components, these other components. More particularly, 12 components marked with "*" in Table 1 are those components to be newly analyzed that were not inspected in the past. Hence, it is desirable that these new 12 components be analyzed simultaneously with existing 41 components, with individual peaks being separable. In other words, the ability to analyze all 53 amino acids at the same time is now needed.

TABLE 1

List of 53 amino acid components

| No. | Abbreviation | Added Component | Name of Amino Acid Component in Body Fluid (English Language) |
|---|---|---|---|
| 1 | P.Ser | | Phosphoserine |
| 2 | Tau | | Taurine |
| 3 | PEA | | Phospho ethanol Amine |
| 4 | Urea | | Urea |
| 5 | Asp | | Aspartic acid |
| 6 | Hypro | | Hydroxy proline |
| 7 | MetSOX | * | Methionine sulfoxides |
| 8 | Thr | | Threonine |
| 9 | Ser | | Serine |
| 10 | AspNH$_2$ | | Asparagine |
| 11 | Glu | | Glutamic acid |
| 12 | GluNH$_2$ | | Glutamine |
| 13 | Sar | | Sarcosine |
| 14 | α-AAA | | α-amino adipic acid |
| 15 | Pro | | Proline |
| 16 | Gly | | Glycine |
| 17 | Ala | | Alanine |
| 18 | Cit | | Citrulline |
| 19 | α-ABA | | α amino-n-butyric acid |
| 20 | Val | | Valine |
| 21 | Pipeco | * | Pipecorinic acid |
| 22 | HCysH | * | Homo cysteine |
| 23 | Met | | Methinine |
| 24 | Hcit | * | Homo citrulline |
| 25 | Allo-Ile | * | Allo isoleucine |
| 26 | Cys | | Cystine |
| 27 | Saccha | * | Saccharopine |
| 28 | Ile | | Isolcecine |
| 29 | Leu | | Leucine |
| 30 | Tyr | | Tyrosine |
| 31 | Cysthi | | Cystachionine |
| 32 | Phe | | Phenylalanine |
| 33 | ASA | * | Arginino saccinic acid |
| 34 | Cys-Hcys | * | Cysteine-Homocysteine mixed disulfides |
| 35 | β-Ala | | β-Alanine |
| 36 | ALevA | * | Amino levulinic acid |
| 37 | β-AiBA | | β-Amino iso butyric acid |
| 38 | γ-ABA | | γ-Amino-n-butyric acid |
| 39 | HCys | * | Homo cystine |
| 40 | ASA-Anhyl | * | Arginino saccinic acid anhydrides 1 |
| 41 | EOHNH$_2$ | | Ethanole amine |
| 42 | Trp | | Tryphophan |
| 43 | NH$_3$ | | Ammonia |
| 44 | Hylys | | Hydroxylysine |
| 45 | AEC | * | Amino ethyl cysteine |
| 46 | Orn | | Ornithine |
| 47 | Lys | | Lysine |
| 48 | 1Mehis | | 1-Metylhistidine |
| 49 | His | | Histidine |
| 50 | 3Mehis | | 3-Metylhisistidine |
| 51 | Ans | | Anserine |
| 52 | Car | | Carnosine |
| 53 | Arg | | Arginine |

However, almost all of these added components are caused to be eluted around a similar range of time when using an existing analyzing method of 41 components. In other words, the elution time is superimposed with those of some of the existing components and a chromatogram does not show a clear separation.

SUMMARY OF THE INVENTION

An object of the invention is to provide a computerized method and apparatus for analyzing amino acids wherein 53 components, including 12 newly found components, can be analyzed simultaneously and efficiently within a short time.

In an object of the present invention a computerized method for analyzing a plurality of amino acids in a fluid sample by a user is provided comprising the steps of introducing the sample into a buffer solution and passing the sample in the buffer solution through a separation column. Further the computerized method provides setting a lithium ion concentration in the buffer to no more than 0.3 mols/L up to a time before β-aminoisobutyric acid (β-AiBA) is eluted and displaying the analysis for the user.

In another object of the present invention, and apparatus for analyzing a plurality of amino acids in a fluid sample by a user is provided comprising a container for supplying a buffer solution, a control valve for controlling a lithium ion concentration and pH of the buffer solution, an auto sampler for supplying the fluid sample and a separation column for separating the plurality amino acids in the buffer fluid sample. The apparatus further provides a processor in communication with the control valve and the auto sampler the processor being programmed for introducing the sample into a buffer solution, passing the sample in the buffer solution through a separation column; setting a lithium ion concentration in the buffer to no more than 0.3 mols/L up to a time before β-aminoisobutyric acid (β-AiBA) is eluted and displaying the analysis for the user.

In yet another object of the present invention a method for analyzing a plurality of amino acids in a fluid sample is provided comprising the steps of introducing the sample into a buffer solution, passing the sample in the buffer solution through a separation column and setting a lithium ion concentration in the buffer to no more than 0.3 mols/L up to a time before β-aminoisobutyric acid (β-AiBA) is eluted.

In another object of the present invention, a computerized method for analyzing a plurality of amino acids in a fluid sample by a user is provided, comprising the steps of introducing the sample into a buffer solution, passing the sample in the buffer solution through a separation column, setting a lithium ion concentration in the buffer to no more than 0.3 mols/L up to a time before β-aminoisobutyric acid (β-AiBA) is eluted, setting a pH to no more than 3.5 for the buffer solution up to a time before the β-aminoisobutyric acid (β-AiBA) is eluted and displaying the analysis for the user.

In yet another object of the present invention, an apparatus for analyzing a plurality of amino acids in a fluid sample by a user is provided comprising a container for supplying a buffer solution, a control valve for controlling a lithium ion concentration and pH of the buffer solution, an auto sampler for supplying the fluid sample and a separation column for separating the plurality amino acids in the buffer fluid sample. The apparatus further provides a processor in communication with the control valve and the auto sampler the processor being programmed for introducing the sample into a buffer solution, passing the sample in the buffer solution through a separation column, setting a lithium ion concentration in the buffer to no more than 0.3 mols/L up to a time before β-aminoisobutyric acid (β-AiBA) is eluted, setting a pH to no more than 3.5 for the buffer solution up to a time before the β-aminoisobutyric acid (β-AiBA) is eluted and displaying the analysis for the user.

In yet another object of the present invention a method for analyzing a plurality of amino acids in a fluid sample is provided comprising the steps of introducing the sample into a buffer solution, passing the sample in the buffer solution through a separation column, setting a pH to no more than 3.5 for the buffer solution up to a time before the β-aminoisobutyric acid (β-AiBA) is eluted and setting a lithium ion concentration in the buffer to no more than 0.3 mols/L up to a time before β-aminoisobutyric acid (β-AiBA) is eluted.

BRIEF DESCRIPTION OF THE DRAWINGS

The above advantages and features of the invention will be more clearly understood from the following detailed description which is provided in connection with the accompanying drawings.

FIG. 3 shows an analysis program of the invention;

FIG. 4 shows a prior-art analysis program;

DETAILED DESCRIPTION OF THE INVENTION

Figure 1:
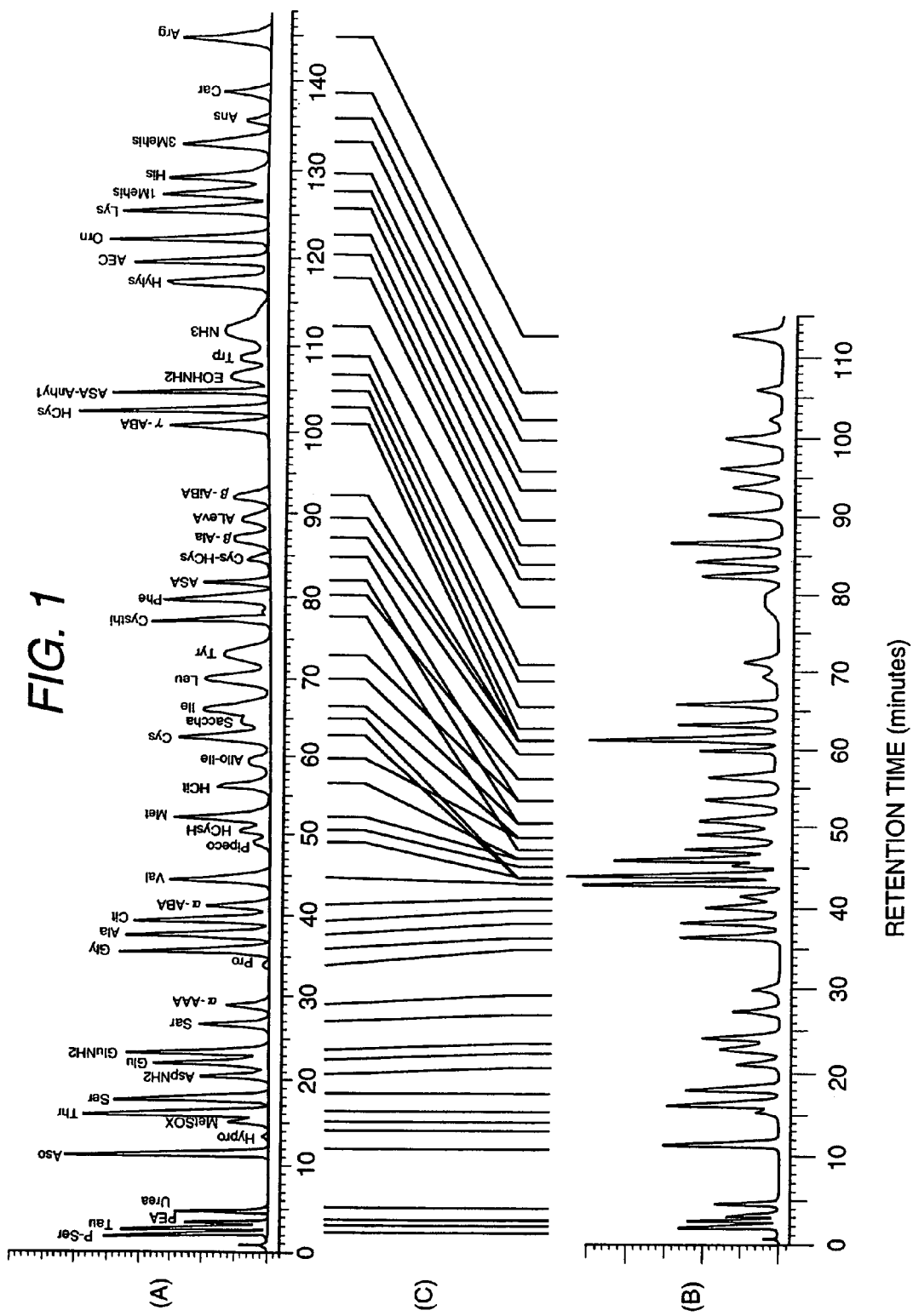
FIG. 1 illustrates a chromatogram wherein 53 amino acid components are separated from one another according to the method of the invention.

Exemplary embodiment of the present invention will be described below in connection with the drawings. Other embodiments may be utilized and structural or logical changes may be made without departing from the spirit or scope of the present invention. Although exemplary process conditions for analyzing the various amino acids are described below, these are only representative and are not meant to be considered as limiting the invention. For instance, variations in temperature and flow rate can be made without effecting the scope of the invention. Further, although the invention is described with respect to 53 amino acids, the invention is applicable for analyzing fewer amino acids, for instance, 50 amino acids. Like items are referred to by like reference numerals throughout the drawings.

Figure 2:
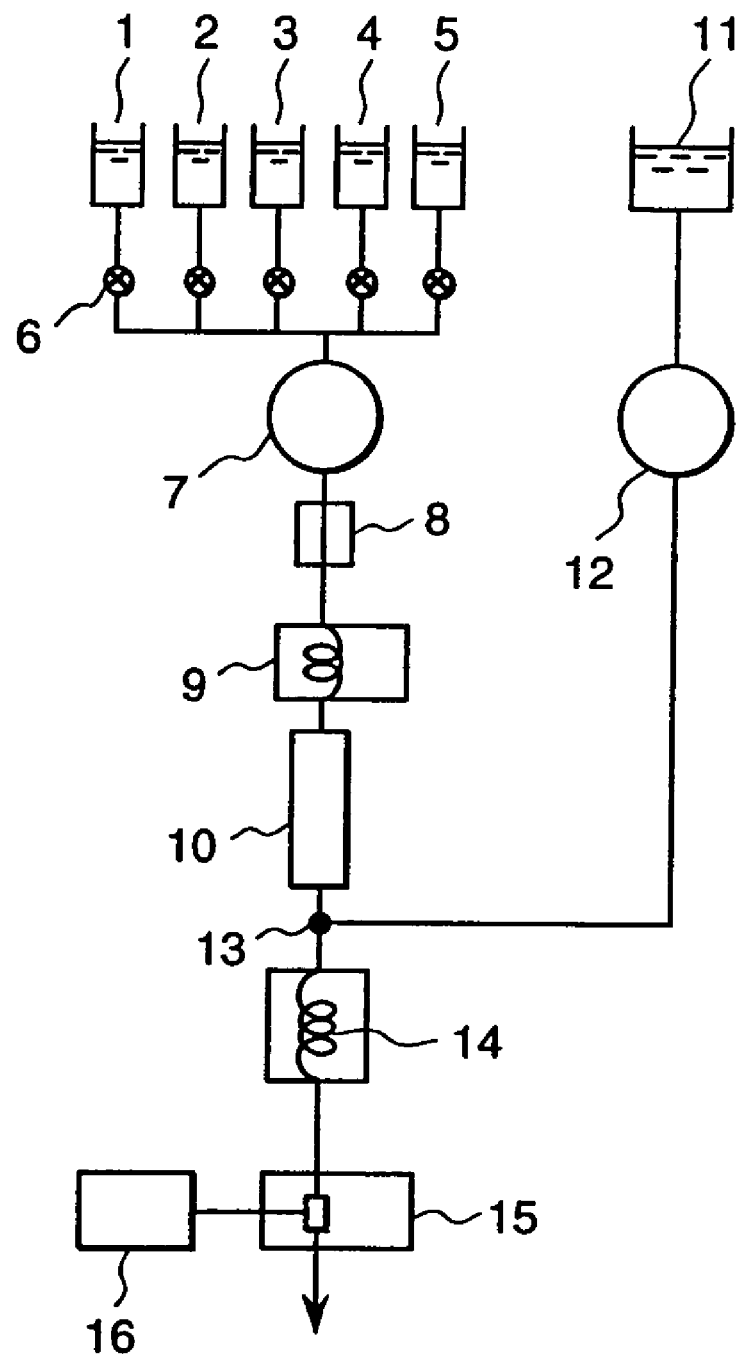
FIG. 2 is an illustrative view of a flow path of an employed apparatus.

Referring now to FIG. 2, a view illustrating an apparatus arrangement and a flow path of an amino acid analyzer according to the invention is shown. Reference numerals 1–4, respectively, indicate first-fourth buffer solutions in a buffer container, and reference numeral 5 indicates a column regenerant. Among these buffer solutions, one buffer solution is selected by means of a series of electromagnetic control valves 6, and fed by means of a buffer solution pump 7 via an ammonia filter column 8 and an auto sampler 9 to a separation column 10. The amino acid sample introduced from the auto sampler 9 is separated in the separation column 10. The separated amino acids are individually mixed with a ninhydrin reagent 11, passed by means of a ninhydrin pump 12, in a mixer 13, followed by reaction with the aid of a heated reaction coil 14. The amino acid that develops a color as a result of the reaction is continuously detected in a detector 15, thereby outputting a chromatogram and data from a data processor 16, followed by recording and storage.

For the buffer solution and column regenerant, commercially available products were used, for example, L-8500-PF-KIT (Mitubishi Chem. Co., Ltd.) (Table 2). The ninhydrin reagent 11 used was a commercially available ninhydrin liquid reagent L-8500 set (made by Wako Jyunyaku Ind. Co., Ltd.) 4.6 mm ID×60 mm packed column was used as the separation column 10, and ion exchange resin 2622 SC (Made by Hitachi, Ltd.) was used as a filler.

TABLE 2

Compositions of buffer solutions

| Name | B1 | B2 | B3 | B4 | B5(RG) |
|---|---|---|---|---|---|
| Lithium ion concentration (mols/L) | 0.09 | 0.255 | 0.721 | 1.00 | 0.20 |
| Lithium citrate (4H$_2$O) (g) | 5.73 | 9.80 | 8.79 | 9.80 | |
| Lithium chloride (g) | 1.24 | 6.36 | 26.62 | 38.15 | |
| Citric acid (g) | 19.90 | 12.0 | 11.27 | 3.30 | |
| Lithium hydroxide (g) | | | | | 8.40 |
| Ethanol (ml) | 30.0 | 30.0 | 100.0 | | 30.0 |
| Benzyl alcohol (ml) | | | 3.0 | | |
| Thiodiglycol (ml) | 5.0 | 5.0 | | | |
| BRIJ-35 (g) | 1.0 | 1.0 | 1.0 | 1.0 | 1.0 |
| Capric acid (ml) | 0.1 | 0.1 | 0.1 | 0.1 | 0.1 |
| pH | 2.8 | 3.7 | 3.6 | 4.1 | |
| Total amount (L) | 1.0 | 1.0 | 1.0 | 1.0 | 1.0 |

Figure 5A:
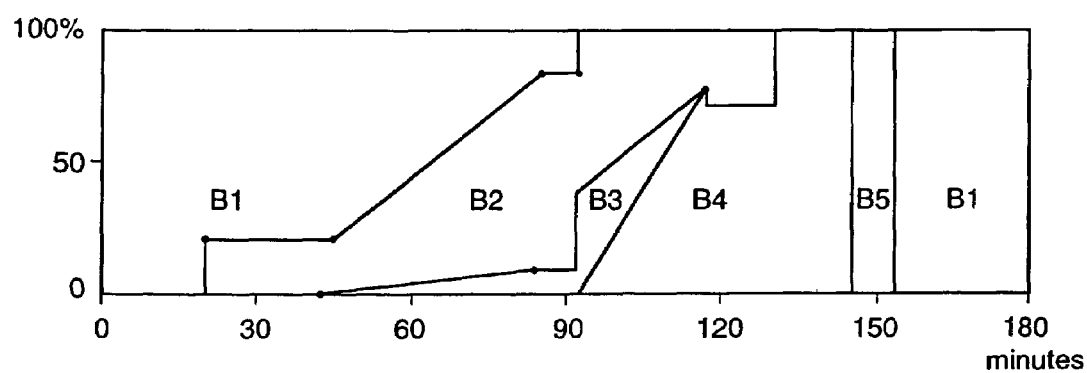
FIGS. 5(A) and 5(B) illustrate a graph of the analysis program of FIG. 3(A) and a graph of the analysis program of FIG. 4(B)

The analysis program of the invention is shown in FIG. 3. The diagram of the gradient mixing program of the buffer solutions of FIG. 3 is shown in FIG. 5(A). The columns of "% B1–%B5", respectively, correspond to first buffer solution 1—column regenerant 5. The value of 100.0 at the columns of "%B1–%B5" at 0 hour means that a corresponding electromagnetic control valve is opened at 100%. Likewise, the values of 80 and 20 mean that corresponding two electromagnetic valves are opened by time ratio at 80% and 20%, respectively, i.e. the solutions are mixed at 80% and 20%. Moreover, when the mixing ratio is changed with time, gradient mixing is enabled. When using the arrangement of FIG. 1, a gradient of up to 5 possible solutions is allowable.

The "temperature" indicates a temperature program of a separation column. The figure "38" means to constantly keep the temperature at 38° C. before a next designated time.

The term "Flow Rate 1" means a flow rate of a pump for the buffer solution and the term "Flow Rate 2" means a flow rate of a ninhydrin pump.

The columns of "%R1–%R3" indicate mixing ratios of the ninhydrin reagents, respectively. Usually, the ninhydrin reagent is commercially available in the form of two solutions and R1 and R2 are mixed at 50%:50% in practice. Distilled water is set as R3, which is used for washing after completion of the analysis.

Figure 5B:
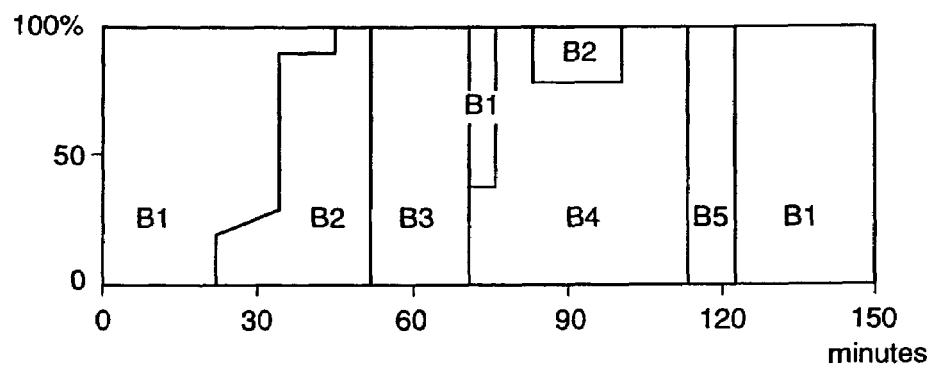

Now, a conventionally employed analysis program is shown in FIG. 4. FIG. 5(b) shows the gradient mixing program of the buffer solutions of FIG. 4. As will be apparent from FIG. 5, the buffer solutions of the conventional case are fundamentally changed over in a stepwise manner. In the practice of the invention, although the total analysis time is elongated, gradients are frequently used, and buffer solutions are changed gently one by one.

In FIG. 1(A), there is shown an analytical chromatogram obtained by use of the analysis program of FIG. 3. FIG. 1(B) shows a chromatogram obtained according to the conventional analysis program of FIG. 4. Both chromatograms are those obtained by measurement of 53 components of the amino acid samples indicated in Table 1. It will be noted that abbreviations of the components are given at individual peaks in FIG. 1(A), and reference should be made to Table 1 wherein the abbreviations indicated in the chromatograms are set out. FIG. 1(C) indicates lines connecting peaks of corresponding components in the chromatograms of FIGS. 1(A) and 1(B), respectively.

Figure 6:
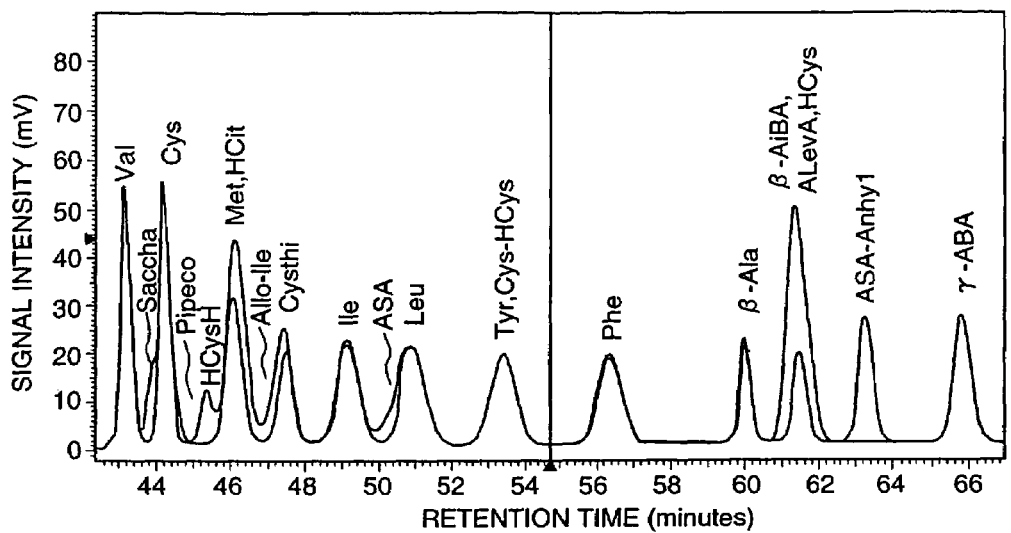
FIG. 6 is an enlarged view of part of the chromatogram of FIG. 5(B)

As will be seen from FIG. 1, a number of components exist between Val-γ-ABA components in FIG. 1(B), not permitting good separation. A portion corresponding to the area between Val-γ-ABA in FIG. 1(B) is shown, as enlarged, in FIG. 6. A number of components whose peaks are superposed are observed including Saccha and Cys, Tyr and Cys-Hcys, and the like. In contrast, it will be seen from FIG. 1(A) that individual components are well separated from one another.

Next, as shown in FIG. 1(A), the procedure of producing the analysis program according to the invention wherein 53 components can be analyzed at the same time is described.

First, with respect to factors for ensuring good peak separation of individual components, where a separation column is fixed and the formulations of buffers solutions are fixed as those indicated in Table 2, the following factors may be considered.

1. Movement of a peak position by the influence of the strength of a Li ion concentration.

2. Movement of a peak position by the influence of the strength of pH.

3. Movement of a peak position by the influence of the column temperature.

4. Combinations of 1, 2 and 3 above.

Also, the flow rate of a buffer solution pump is considered, but is not set out herein. It is well known that when the flow rate of the buffer solution pump is doubled, for example, the analytical time can be reduced substantially proportionally to ½. In this connection, it is also known that separation between adjacent peaks is worsened as a whole. In other words, the flow rate can be altered without departing from the scope of the invention. In this regard, other test conditions, such as temperature, can also be altered without departing from the scope of the invention.

Based on the factors set out above, it is considered to improve the separation according to the following procedures.

a: A given mixing ratio or gradient mixing ratio of buffer solutions is changed.

b: The time of commencing the change-over of a given mixing ratio or gradient mixing ratio of buffer solutions is changed.

c: The time of completing the change-over of a given mixing ratio or gradient mixing ratio of buffer solutions is changed.

d: The given mixing ratio or gradient mixing ratio of buffers solutions is determined using three or more solutions.

e: The column temperature is changed.

f: The commencing time of the change-over of the column temperature is changed.

g: The completion time of the change-over of the column temperature is changed.

h: Combinations of a–g above.

Specific examples of improving the separation by use of the above procedures are described with reference to FIGS. 9–17.

It should be noted that the analysis program times (including a change-over time of buffer solution, a change-over time of column temperature and the like) are based on the time at the electromagnetic valves 6 in FIG. 2 and are thus different from the times (retention times) at which individual components are eluted as indicated in the chromatogram. The analysis program times and the retention times, respectively, have a time lag corresponding to a time during which a buffer solution passes from the electromagnetic control valve series 6 to the detector 15, particularly with a time lag of about 5–15 minutes.

Figure 9:
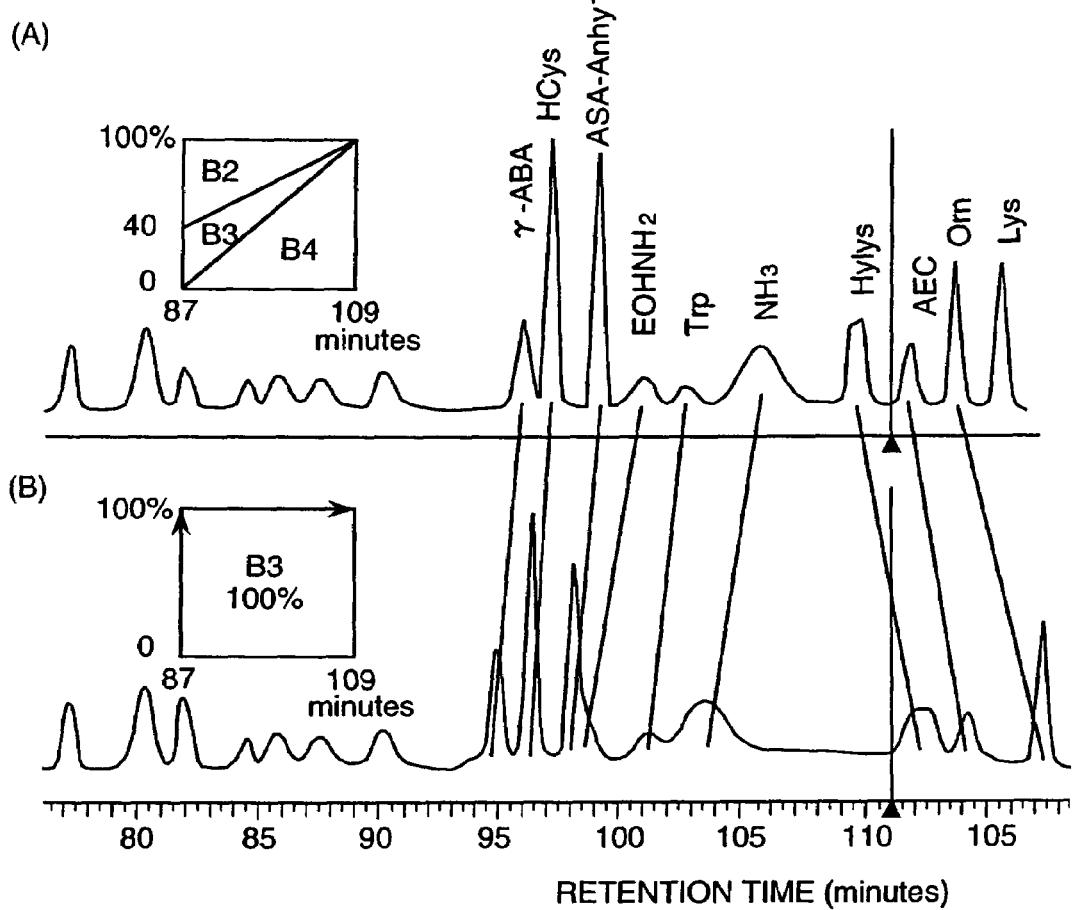
FIG. 9 illustrates the state of separation wherein three buffer solutions are subjected to a gradient within a time frame of 87 minutes–109 minutes (A), and the state of separation in case of buffer solution B3=100% (B)

FIG. 9 illustrates the state of separation wherein three buffer solutions are subjected to a gradient within a time frame of 87 minutes–109 minutes (A), and the state of separation in case of buffer solution B3=100% (B). From FIG. 9, it will be seen that the case where the gradient of three-solutions of B2, B3 and B4 ensures well-balanced separation over γ-ABA-Lys. Especially, good separation between ASA-Anhy1 and EOHNH$_2$ is observed. This means that the lithium ion concentration and the pH that are, respectively, increased in a gradient way (Li concentration: 0.441 mols/L→1.00 mol/L, pH: 3.66→4.1) is better than those that are constant at the B3 level (Li concentration: 0.721 mols/L, pH: 3.6).

Figure 10:
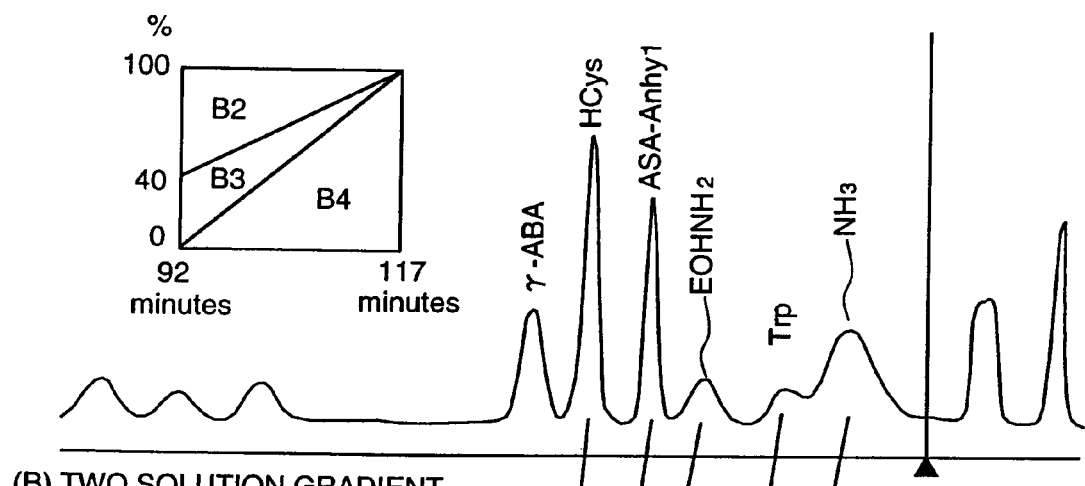
FIG. 10 illustrates the case where three solutions of B2–B4 are subjected to gradient within a time of 92 minutes–117 minutes (A) and the state in the case where two solutions of B3 and B4 are subjected to gradient (B)
Figure 10:
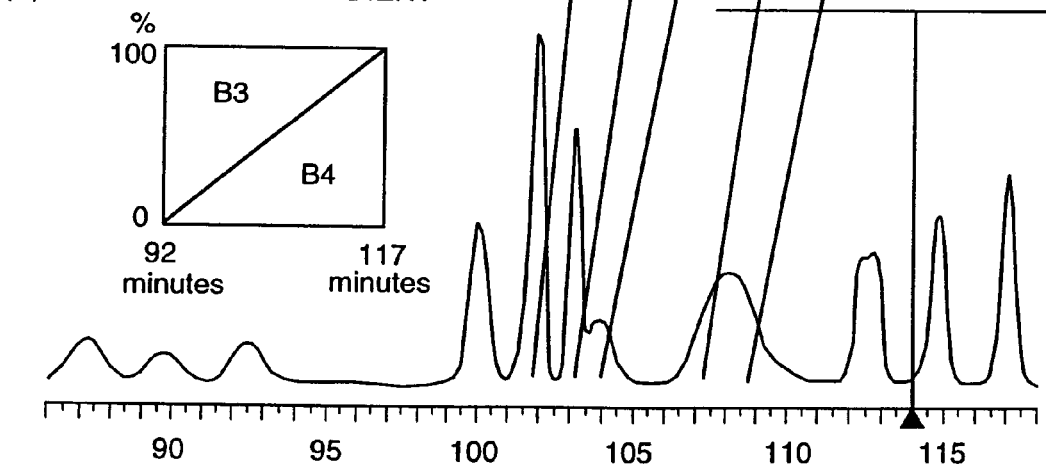

FIG. 10 illustrates the case where three solutions of B2–B4 are subjected to gradient within a time of 92 minutes–117 minutes (A) and the state in the case where two solutions of B3 and B4 are subjected to gradient (B). From FIG. 10, it will be seen that better separation between ASA-Anhy1 and EOHNH$_2$ is obtained in the three solution gradient (A) than in the two solution gradient (B). At the same time, good separation is obtained between Trp and NH$_3$. From the standpoint of the lithium ion concentration and pH, this means that the gradient (A) of Li concentration: 0.441 mols/L→1.00 mol/L, pH: 3.66→4.1 is preferred to the case (B) of Li concentration: 0.721 mols/L→1.00 mol/L, pH: 3.6→4.1.

Accordingly, it will be appreciated that the procedure of using the three solution gradient of B2–B4 provides the best separation balance around γ-ABA-Lys while taking the results of FIG. 9 into consideration. In the analysis program of the invention, the three solution gradient of B2–B4 is used within 92 minutes–117 minutes based on the above results.

Figure 11:
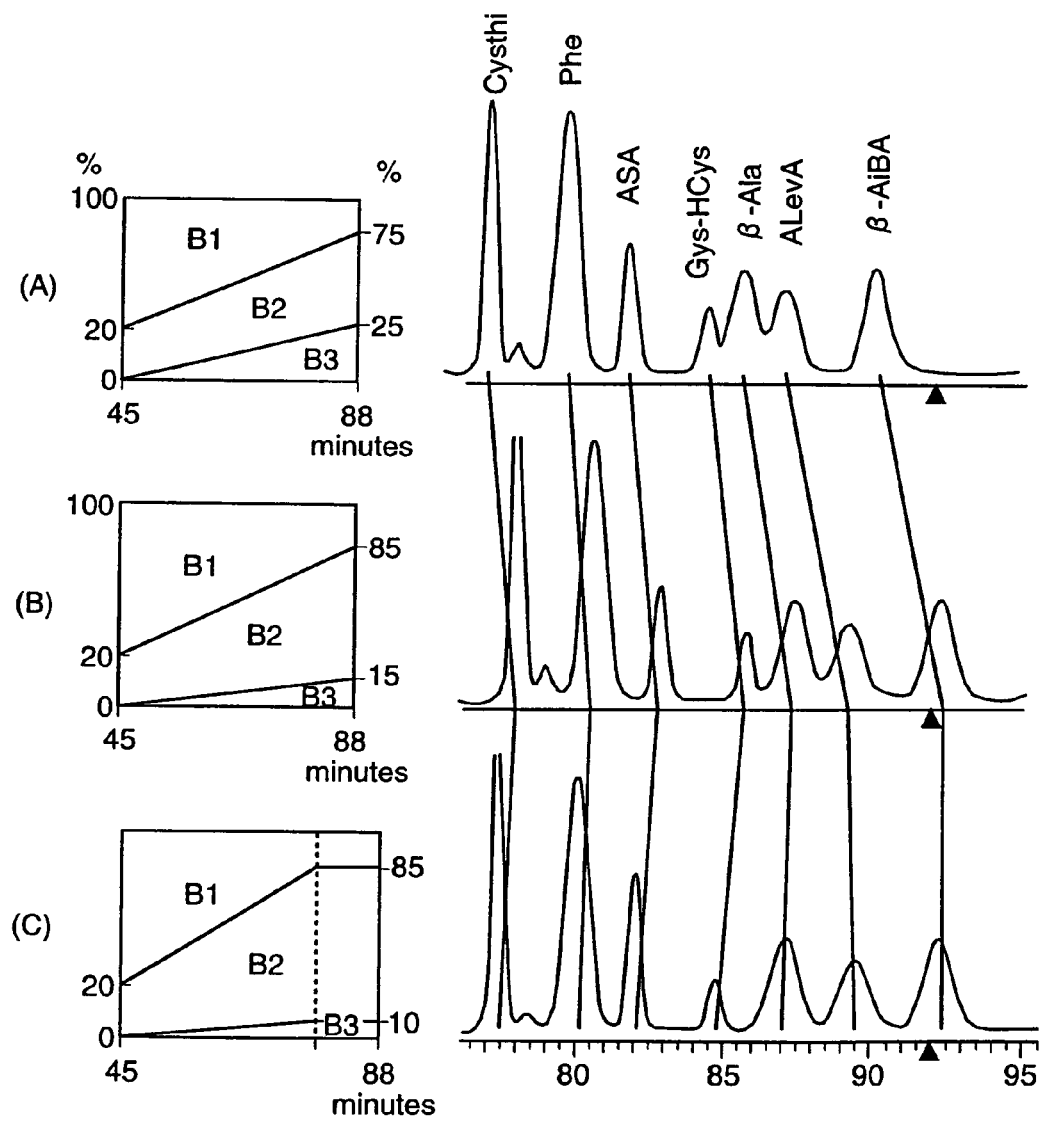
FIG. 11 illustrates how separation is improved for different gradients of B3.

FIG. 11 illustrates the separation improvement using a gradient of B3 starting from 45 minutes. It will be seen that when the gradient is reduced from 25% (A) to 10% (C), the separation between Phe-β-AiBA is well balanced. The change in the lithium ion concentration is such that 0.123→0.277 mols/L for (C), 0.123→0.280 mols/L for (B), and 0.123→0.316 mols/L for (A). The results reveal that individual peaks are separated from one another in state (B), and are not fully separated in state (A). From this, it may be said that when the lithium ion concentration is 0.30 mols/L or over, the separation balance between Phe-β-AiBA is poor and thus, is inconvenient. Accordingly, in the analysis program of the invention, the state of (A) is intended, and B3 is so set as to have a 10% gradient over a time of from 45 minutes to 84 minutes. In addition, the composition at the time of 84 minutes is not changed up to 92 minutes.

Figure 12:
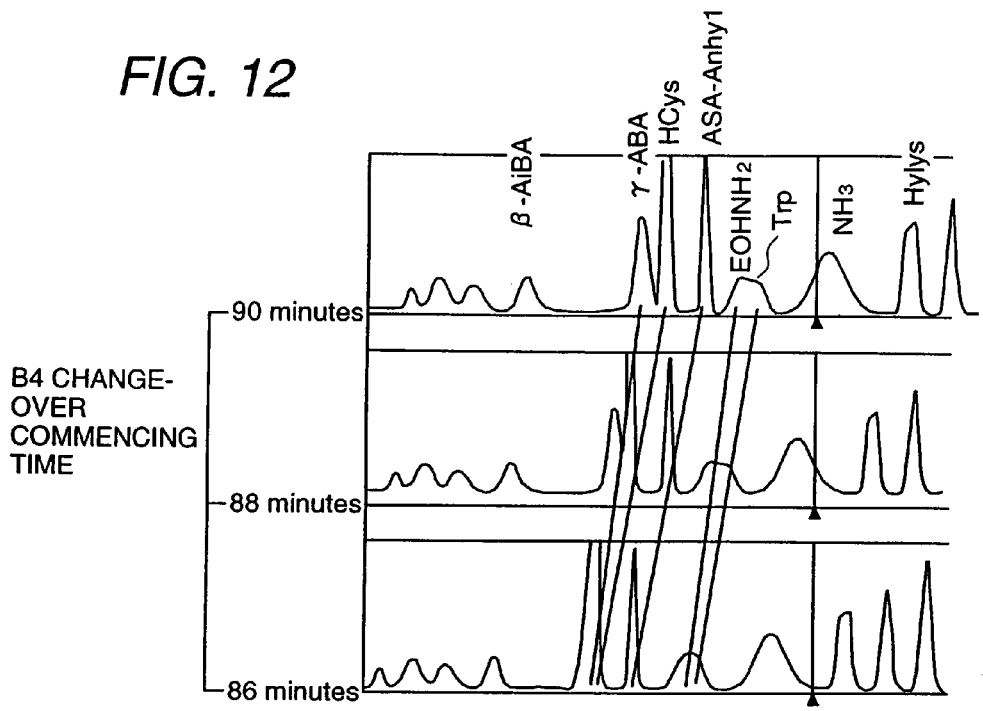
FIG. 12 illustrates the state where a gradient commencing time of buffer solution B4 is changed within 86 minutes–90 minutes.

FIG. 12 illustrates the gradient commencing time of buffer solution B4 as it changes between 86 minutes–90 minutes. It will be seen that as shown in FIG. 12, when the gradient commencing time of buffer solution B4 is delayed, γ-ABA and Hcys are separate from each other, with an improvement in separation between EOHNH2 and Trp. Thus, according to the analysis program of the invention, B4 is switched over from 92 minutes.

Figure 13:
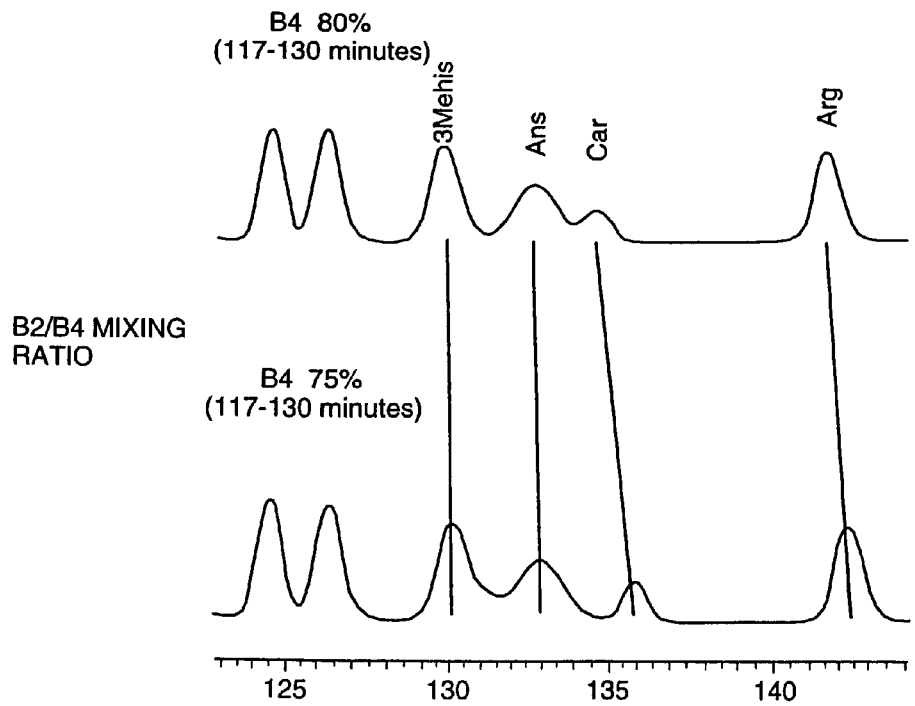
FIG. 13 illustrates the case where a mixing ratio of B3 and B4 is changed.

FIG. 13 shows the results of the study on the mixing ratio of B2 and B4 in the course of 117–130 minutes. As will be seen from FIG. 13, when the ratio of B4 is reduced from 80% to 75%, the separation between Ans and Car is improved. As for the lithium ion concentration and pH, Li concentration: 0.851 mols/L and pH: 4.02 for the B4 ratio of 80%, and Li concentration: 0.814 mols/L and pH: 4.00 for the Br ratio of 75%. Thus, according to the analysis program of the invention, the mixing ratio of B2 and B4 during 117–130 minutes is set at 1:3 (i.e. a rate of B4 of 75%).

Figure 14:
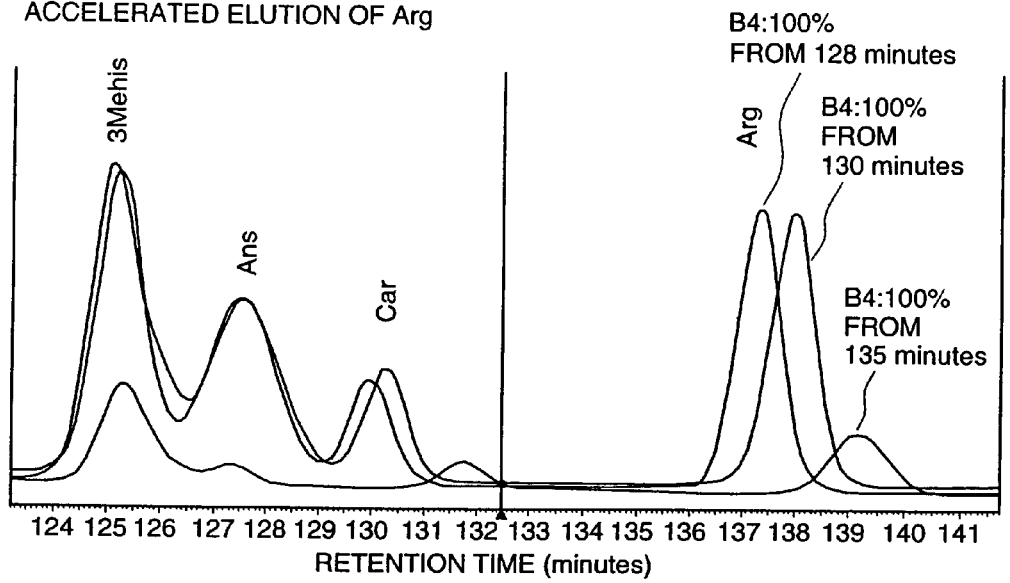
FIG. 14 illustrates the results of a test where a commencing time of change-over of B4 to 100% bias delayed from 128 minutes to 135 minutes.

FIG. 14 illustrates the commencing time at which B4 is changed over to 100% is delayed from 128 minutes to 135 minutes. This shows that when the change-over time is delayed, the separation between Ans and Car is improved, but the elution time of Arg is delayed. Accordingly, in the analysis program of the invention, the commencing time at which B4 is changed over to 100% starts from 130 minutes while taking a total balance into account.

Figure 15:
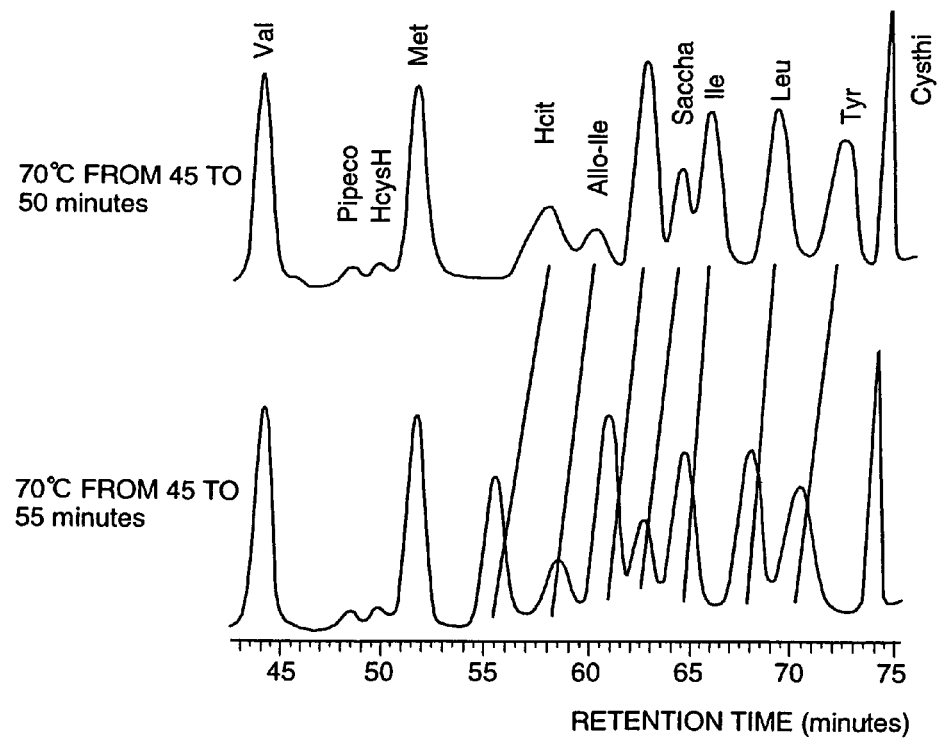
FIG. 15 illustrates an improvement in separation over Met-Cysthi depending on the column temperature.
Figure 16:
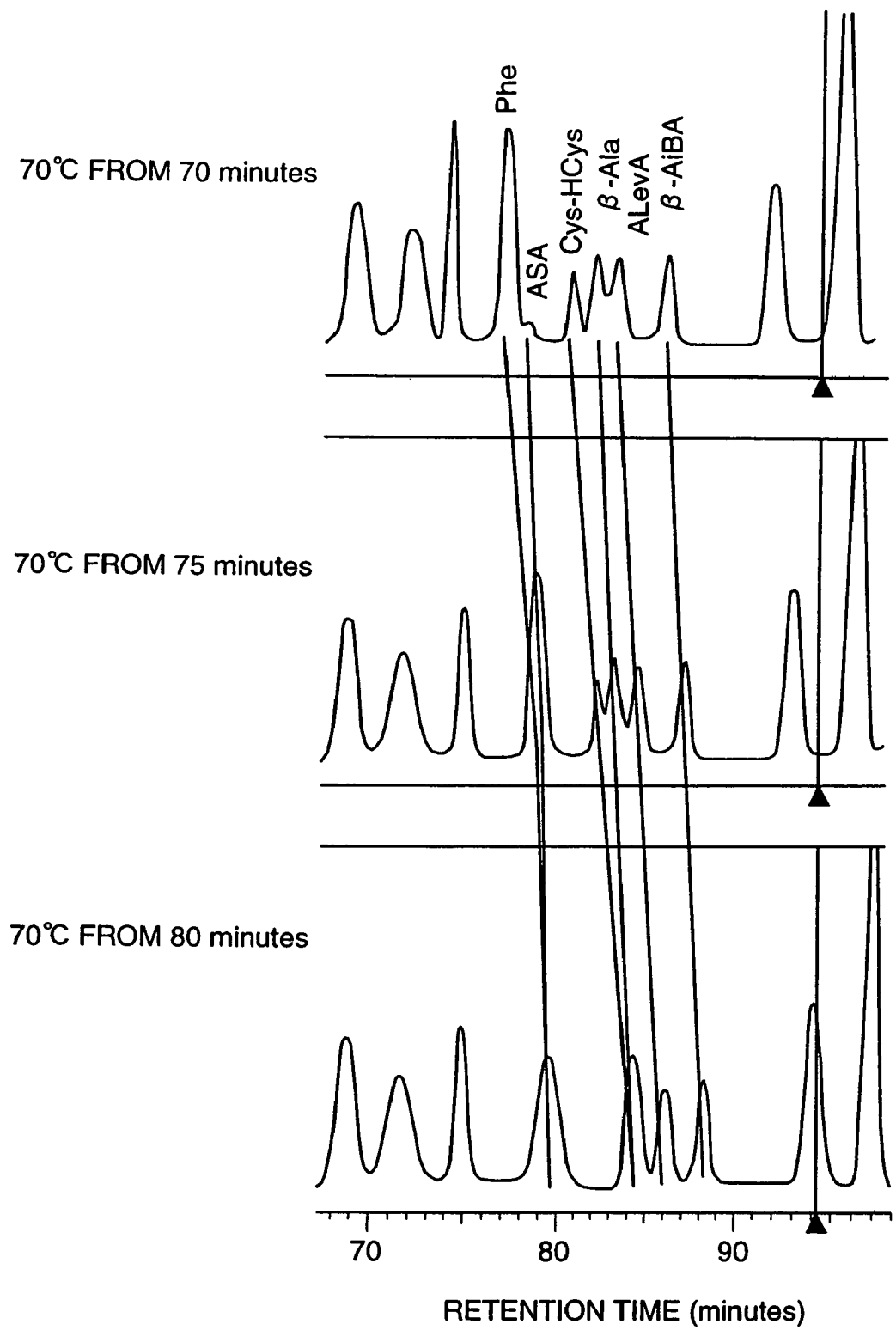
FIG. 16 illustrates an improvement in separation over Phe-β-AiBA when the commencing time of switching a column temperature is changed.
Figure 17:
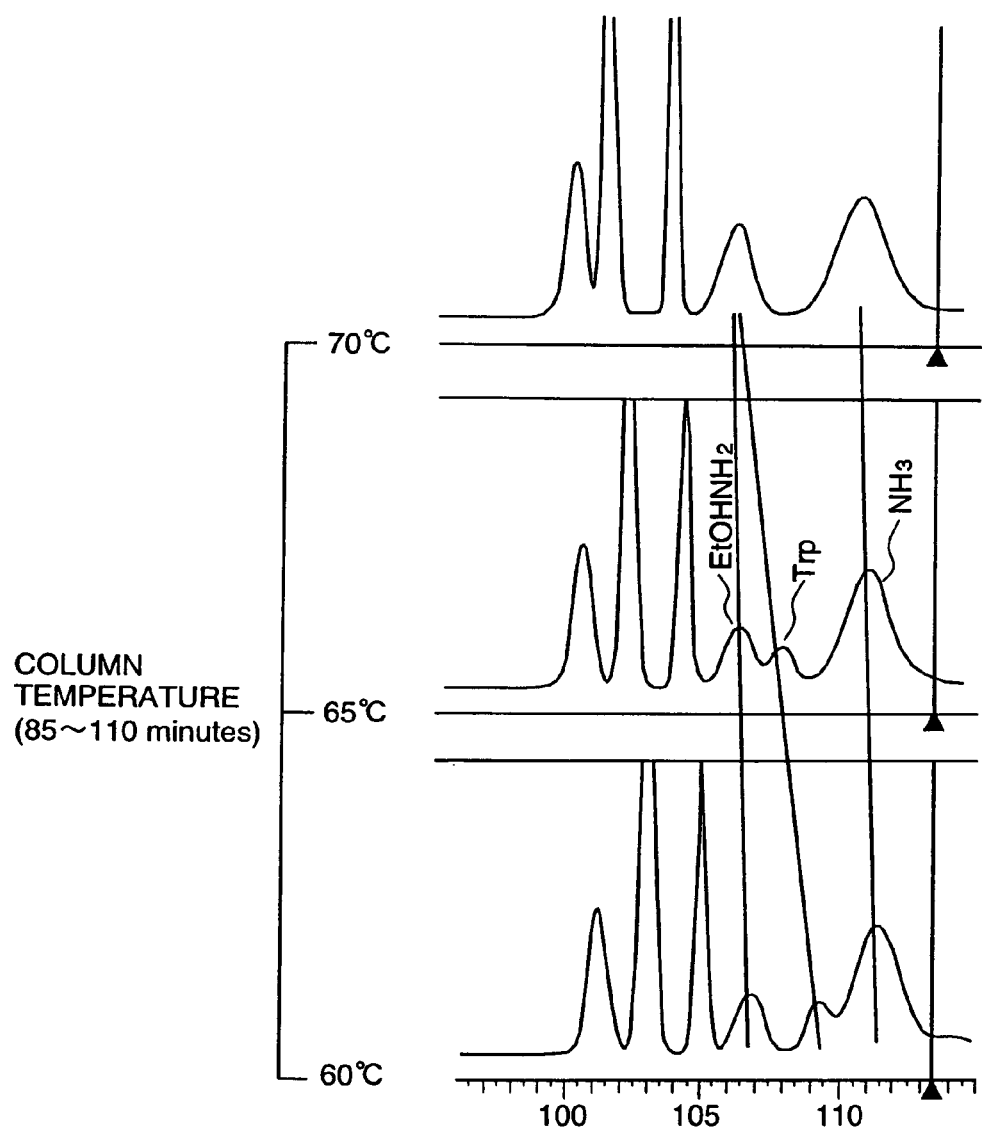
FIG. 17 illustrates the state of the case where the column temperature is decreased from 70° C. to 60° C. in the course of 85 minutes–110 minutes.
Figure 18:
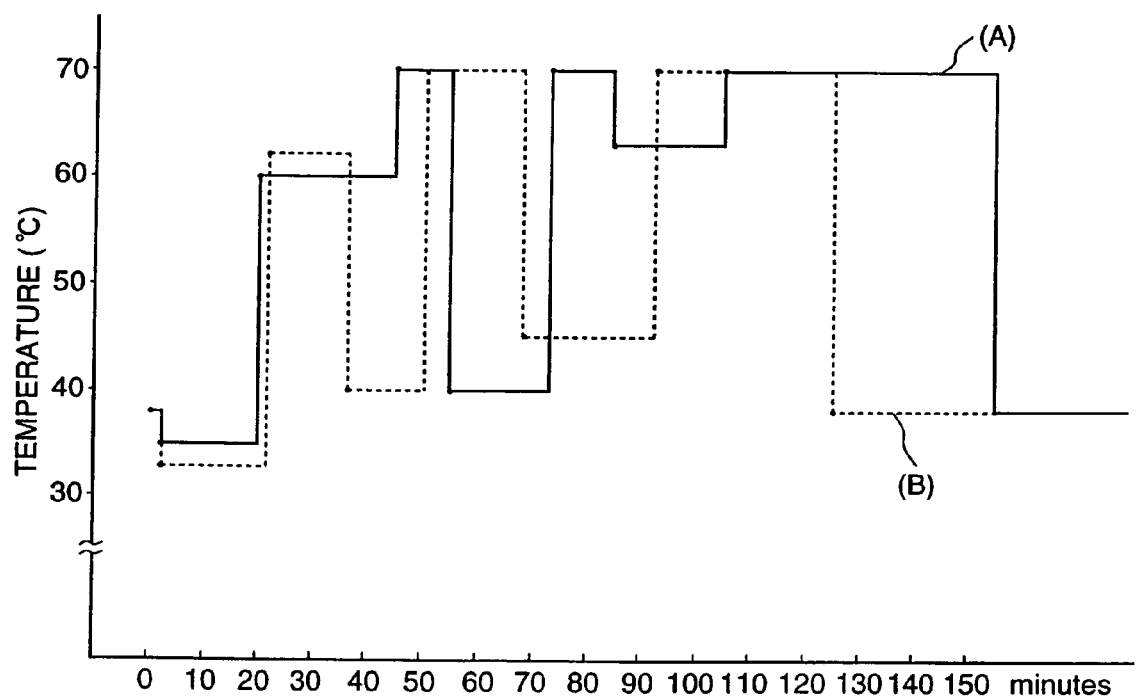
FIG. 18 is a graph illustrating the change of a column temperature in the analysis programs of the invention and prior art, respectively.

The composition of buffer solutions has been hereinabove discussed, and the results of the study on the column temperature are shown in FIGS. 15–17. The change in the column temperature is depicted as a graph in FIG. 18. In FIG. 18, solid line (A) indicates an analysis program of the invention shown in FIG. 4, and broken line (B) is for a conventional analysis program of FIG. 4 shown for reference.

FIG. 15 shows the results of a test of improving the separation between Met-Cysthi depending on the column temperature. The test was conducted such that the time within which the column temperature is set at 70° C. ranges between 45 minutes–50 minutes and also 45 minutes–55 minutes in the analysis program. As a consequence, it has been found that with the range of 45 minutes–55 minutes, the separation is improved in a well-balanced way. Accordingly, in the analysis program of the invention, the column temperature is set at 70° C. within 45 minutes–55 minutes.

FIG. 16 shows the results of a test of improving the separation between Phe-β-AiBA when the time of commencing the change-over of column temperature is changed. When the commencing time at which the column temperature is changed over to 70° C. is sped up from 80 minutes to 70 minutes, the separation is improved. Accordingly, in the analysis program of the invention, it is adopted to commence the change-over of the column temperature to 70° C. at 73 minutes.

FIG. 17 illustrates an example where the column temperature is changed within a range of 70–60° C. in 85 minutes–110 minutes. It will be seen that when the column temperature decreases, the separation between EOHNH$_2$ and Trp is improved. Accordingly, in the analysis program of the invention, the temperature of 63° C. is adopted within a time range of 85 minutes–110 minutes.

The analysis program of the invention shown in FIGS. 3 and 5(A) is determined from the combination of the improvements in the partial separations shown in FIGS. 9–17. Thus, the results of the separation of FIG. 1(A) are realized.

In the analysis program of the invention described above, a plurality of buffer solutions are mixed and the column temperature is controlled. Nevertheless, great factors for good separation of the peaks of 53 components include, as stated hereinbefore, "the strength of Li ion concentration", "the strength of pH", and "the column temperature". The changes of the Li ion concentration and the pH along the analysis program are shown in FIGS. 7 and 8.

Figure 7:
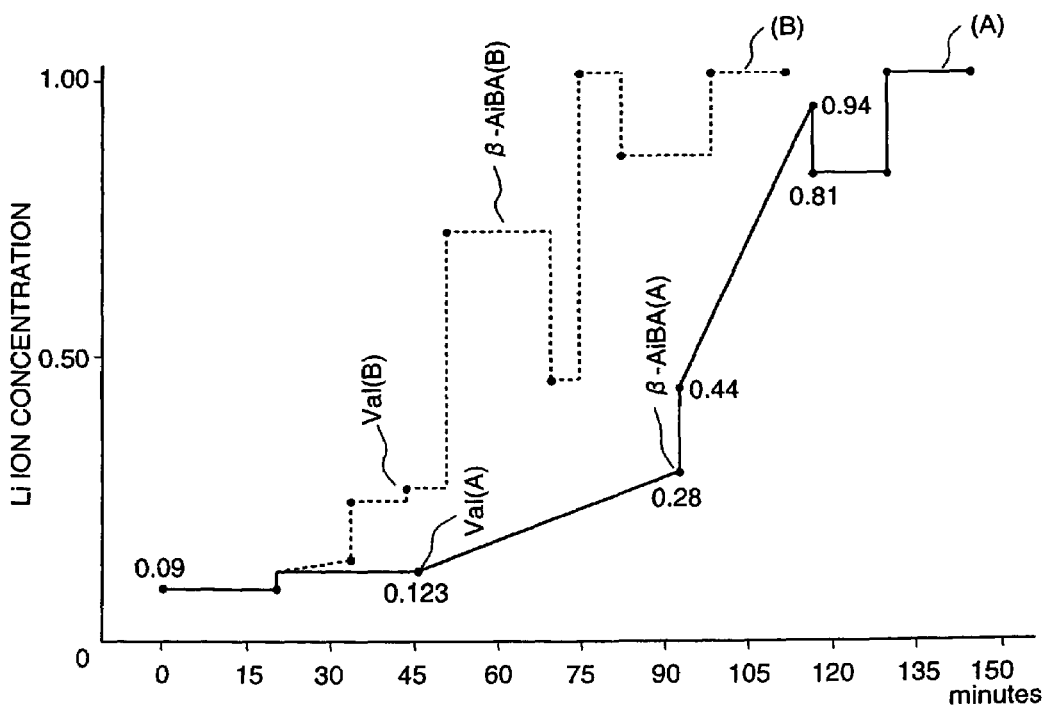
FIG. 7 is a graph of a lithium ion concentration in the analysis program of the invention.

FIG. 7 is a graph showing the change of the Li ion concentration in the inventive and prior art analysis programs. Solid line (A) is for the analysis program of the invention shown in FIG. 3 and broken line (B) is for the prior art analysis program of FIG. 4. As will be seen from the graph, the inventive program shown as (A) is very slow in the rise of the Li ion concentration and gradually increases in comparison with the prior art program (B).

Figure 8:
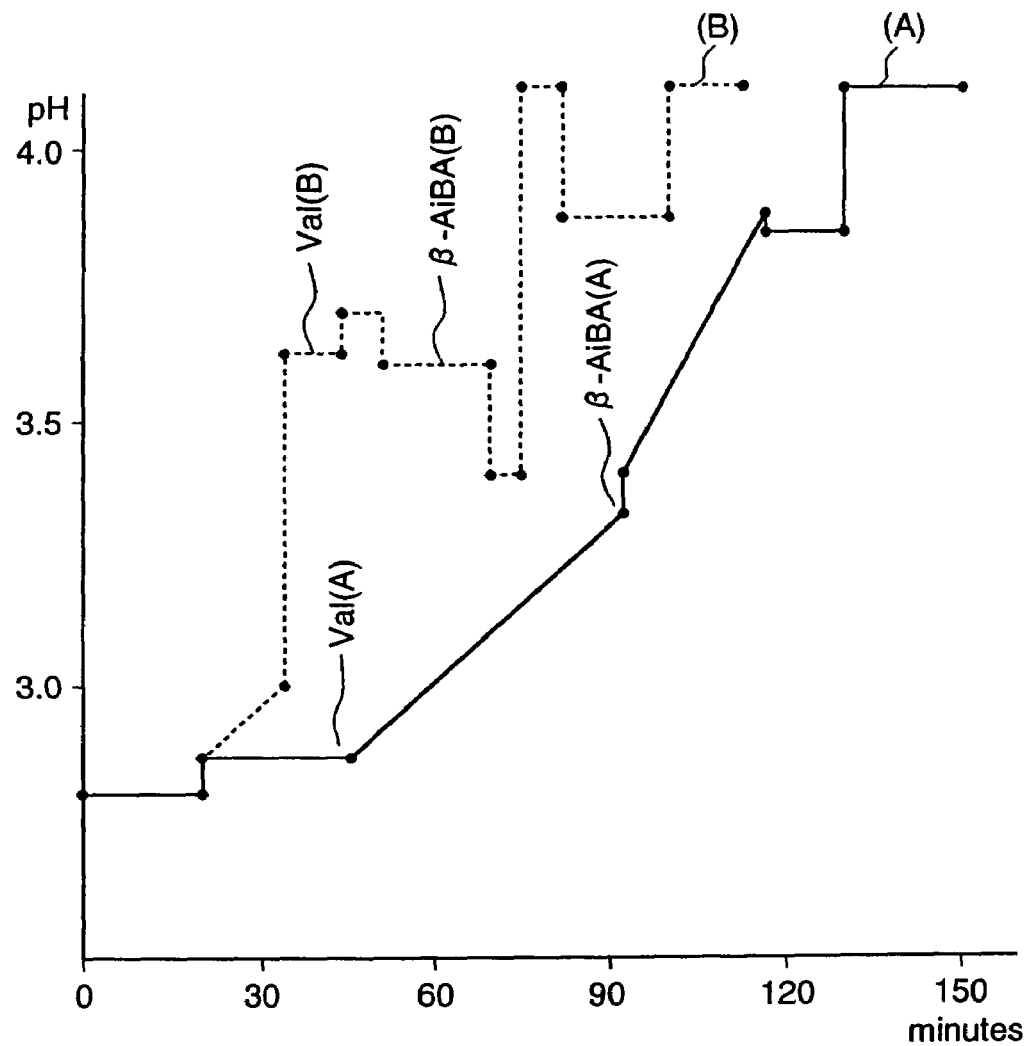
FIG. 8 is a graph of a pH in the analysis program of the invention.

FIG. 8 is a graph showing the results of measurement of a pH change wherein, like FIG. 7, (A) corresponds to the analysis program of the invention in FIG. 3 and (B) corresponds to the prior art analysis program of FIG. 4. In the analysis program of the invention, significant rise in pH is suppressed.

The analysis program of the invention can be summarized as follows on the basis of the partial separation improvements shown in FIGS. 9–17.

1. In order to improve the balance of separation between γ-ABA-Lys, the Li concentration is increased from 0.44 mols/L to 1.00 mols/L and the pH is increased from 3.66 to 4.1, both in a gradient fashion. In the practice of the invention, this is performed according to a three solutions gradient. The three solutions gradient is carried out for a time (retention time) during which β-AiBA to Hylys are eluted while taking the lag of the retention time with the analysis program into account. In the analysis program of the invention, the time is between 87 minutes–109 minutes.

2. In order to improve the balance in the separation between Phe-β-AiBA, the gradient is manipulated so that the Li concentration is set at 0.30 mols/L or below. More particularly, taking the lag of the retention time with the analysis program into consideration, the gradient of buffer solution B3 is kept at 10% at the time (retention time) during which val to β-AiBA are eluted, and the Li concentration is set at 0.30 mols/L or below when β-AiBA is eluted. In the analysis program of the invention, this operation takes about 45 minutes–92 minutes.

3. In order to improve the balance in the separation between γ-ABA and Hcys the gradient commencing time of buffer solution B4 starts from a time (retention time) at which β-AiBA is eluted (while taking the lag of the retention time with the analysis program into consideration). In the analysis program of the invention, the commencement starts from 92 minutes.

4. In order to improve the balance in separation between Ans and Arg, the Li concentration is set at 0.81 and the pH is at 4.00. In the practice of the invention, this is carried out by mixing B2 and B4 (a ratio of B4 of 75%). The time for setting the above-defined Li concentration and pH is determined as a time (retention time) of eluting from Hylys to His while taking the lag of the retention time with the analysis program into consideration. In the analysis program of the invention, this time is between 117 minutes–130 minutes.

After the elution of His (after 130 minutes in the analysis program), buffer solution B4 is used at 100%, under which the Li concentration is set at 1.00 mol/L and the pH is at 4.1.

5. In order to improve the balance in separation between Met-Cysthi, the column temperature is kept at 70° C. during the course of the elution time of val to Hcit (45 minutes–55 minutes in the analysis program) while taking the lag of the retention time with the analysis program into consideration.

6. In order to improve the balance in separation between Phe-β-AiBA, the column temperature is changed over to 70° C. during the course of the elution time of Tyr (73 minutes in the analysis program) while taking the lag of the retention time with the analysis program into consideration.

7. In order to improve the balance in separation between EOHNH$_2$ and Trp, the column temperature is kept at 63° C. during the course of the elution time of from Cys-Hcys to Trp (85 minutes–110 minutes in the analysis program) while taking the lag of the retention time with the analysis program into consideration.

As described above, to ensure the individual separation of 53 components, suppression of the Li ion concentration and the pH to low levels, at least, up to the elution time of β-AiBA is maintained. This leads to a remarkable improvement in the separation balance at portions where peaks most densely appear. The effects obtained by the adoption of the analysis program of the invention can be summarized as follows.

1) Optimization of the buffer solution change-over time permits peaks of individual components to be separated from one another in a well-balanced way when 53 components are analyzed at the same time, and ensures an analysis time reduced to 148 minutes.

2) Such buffer solutions as used in prior art can be used as they are without changing the formulations of the buffer solutions.

3) 53 components can be separated by improving the analysis program alone without altering the hardware or separation column of an analyzer.

Hence, a method for analyzing a plurality of amino acids in a fluid sample by a user is provided comprising the steps of introducing the sample into a buffer solution, passing the sample in the buffer solution through a separation column and setting a lithium ion concentration in the buffer to no more than 0.3 mols/L up to a time before β-aminoisobutyric acid (β-AiBA) is eluted.

Although the invention has been described above in connection with exemplary embodiments, it is apparent that many modifications and substitutions can be made without departing from the spirit or scope of the invention. For instance, variations in flow rate and temperature can be made without departing from the scope of the invention. Accordingly, the invention is not to be considered as limited by the foregoing description, but is only limited by the scope of the appended claims.

What is claimed as new and desired to be protected by Letters Patent of the United States is:

1. An apparatus for analyzing a plurality of amino acids in a fluid sample by a user comprising:
   a container for supplying a buffer solution;
   a control valve for controlling a lithium ion concentration and pH of said buffer solution;
   an auto sampler for supplying said fluid sample;
   a separation column for separating said plurality amino acids in said buffer fluid sample;

a processor in communication with said control valve and said auto sampler; and an analysis program residing on said processor for causing said processor to perform the acts of:
introducing said sample into a buffer solution;
passing said sample in said buffer solution through a separation column;
setting a lithium ion concentration in said buffer to no more than 0.3 mols/L up to a time before β-aminoisobutyric acid (β-AiBA) is eluted; and
displaying said analysis for said user.

2. The apparatus of claim 1 wherein the analysis program causes the processor to further perform the act of setting a pH to no more than 3.5 for said buffer solution up to a time before said β-aminoisobutyric acid (β-AiBA) is eluted.

3. The apparatus of claim 1 wherein the analysis program causes the processor to further perform the act of setting said lithium ion concentration and a pH in said buffer solution to increase in a gradient fashion within a time of eluting from γ-amino-n-butyric acid (γ-ABA) to hydroxylysine (Hylys).

4. The apparatus of claim 3 wherein the analysis program causes the processor to further perform the act of setting said lithium ion concentration to increase from 0.44 mols/L to 1.00 mol/L and said pH to increase from 3.66 to 4.1 in said buffer solution.

5. The apparatus of claim 1 wherein the analysis program causes the processor to further perform the act of said lithium ion concentration at 0.81 mols/L and a pH at 4.00 in said buffer solution within an elution time from hydroxylysine (Hylys) to histidine (His).

6. The apparatus of claim 5 wherein the analysis program causes the processor to further perform the act of setting the lithium ion concentration at 1.00 mol/L and said pH at 4.1 in said buffer solution after the elution of histidine (His).

7. The apparatus of claim 1 wherein the analysis program causes the processor to further perform the act of setting a column temperature at 70° C. within an elution time from valine (val) to homocitrulline (Hcit).

8. The apparatus of claim 1 wherein the analysis program causes the processor to further perform the act of setting a column temperature at 70° C. within an elution time of tyrosine (Tyr).

9. The apparatus of claim 1 wherein the analysis program causes the processor to further perform the act of setting a column temperature at 63° C. within an elution time of from cysteine-homocysteine mixed disulfides (Cys-Hcys) to tryptophane (Trp).

10. The apparatus of claim 1 wherein said plurality of amino acids is selected from the group comprising: phosphoserine (P-Ser), taurine (Tau), phosphoethanolamine (PEA), urea (Urea), asparginic acid (Asp), hydroxyproline (Hypro), methionine sulfoxide (MetSOX), threonine (Thr), Serine (Ser), asparagine (AspNH$_2$), glutamic acid (Glu), glutamine (GluNH$_2$), Sarcosine (Sar), α-aminoadipic acid (α-AAA), proline (Pro), glycine (Gly), analanine (Ala), citrulline (Cit), α-amino-n-butyric acid (α-ABA), valine (Val), pipecolic acid (Pipeco), homocysteine (HCysH), methionine (Met), homocytrulline (HCit), allo-isoleucine (Mo-Ile), cystine (Cys), saccharopin (Saccha), isoleucine (Ile), leucine (Leu), tyrosine (Tyr), cystathionine (Cysthi), phenylalanine (Phe), allgininosuccinic acid (ASA), cysteine-homocysteine mixed disulfides (Cys-Hcys), β-alanine (β-Ala), aminolevulinic acid (ALevA), β-aminoisobutyric acid (β-AiBA), γ-amino-n-butyric acid (γ-ABA), homocystine (HCys), alugininosuccinic acid anhydride 1 (ASA-Anhyl), ethanolamine (EOHNH$_2$), tryptophan (Trp), ammonia (NH$_3$), hydroxylysine (Hylys), aminoethylcysteine (AEC), ornithine (Orn), lysine (Lys), 1-methylhistidine (1Mehis), histidine (His), 3-methylhistidine (3Mehis), anserine (Ans), carnosine (Car) and arginine (Arg).

11. An apparatus for analyzing a plurality of amino acids in a fluid sample by a user comprising:
a container for supplying a buffer solution;
a control valve for controlling a lithium ion concentration and pH of said buffer solution;
an auto sampler for supplying said fluid sample;
a separation column for separating said plurality amino acids in said buffer fluid sample;
a processor in communication with said control valve and said auto sampler; and
an analysis program residing on said processor for causing said processor to perform the acts of:
introducing said sample into a buffer solution;
passing said sample in said buffer solution through a separation column;
setting a lithium ion concentration in said buffer to no more than 0.3 mols/L up to a time before β-aminoisobutyric acid (β-AiBA) is eluted;
setting a pH to no more than 3.5 for said buffer solution up to a time before said β-aminoisobutyric acid (β-AiBA) is eluted; and
displaying said analysis for said user.

\* \* \* \* \*